United States Patent
Bourland, III et al.

(10) Patent No.: US 10,470,757 B2
(45) Date of Patent: *Nov. 12, 2019

(54) SUTURE PASSING INSTRUMENTS AND METHODS

(71) Applicant: Stryker Corporation, Kalamazoo, MI (US)

(72) Inventors: Charles Rice Bourland, III, Coral Gables, FL (US); Johnny J. Valadez, Santa Clarita, CA (US)

(73) Assignee: Stryker Corporation, Kalamazoo, MI (US)

( * ) Notice: Subject to any disclaimer, the term of this patent is extended or adjusted under 35 U.S.C. 154(b) by 275 days.

This patent is subject to a terminal disclaimer.

(21) Appl. No.: 15/479,143

(22) Filed: Apr. 4, 2017

(65) Prior Publication Data

US 2017/0333030 A1    Nov. 23, 2017

Related U.S. Application Data

(63) Continuation of application No. 15/261,521, filed on Sep. 9, 2016, now Pat. No. 9,668,726, which is a (Continued)

(51) Int. Cl.
| | | |
|---|---|---|
| *A61B 17/04* | (2006.01) | |
| *A61B 17/062* | (2006.01) | |
| *A61B 17/06* | (2006.01) | |
| *A61B 17/29* | (2006.01) | |

(52) U.S. Cl.
CPC ...... *A61B 17/0469* (2013.01); *A61B 17/0482* (2013.01); *A61B 17/062* (2013.01); (Continued)

(58) Field of Classification Search
CPC ........... A61B 17/0469; A61B 17/0482; A61B 17/06066; A61B 17/0625; A61B 17/062; A61B 2017/06009; A61B 2017/2926
See application file for complete search history.

(56) References Cited

U.S. PATENT DOCUMENTS

| | | |
|---|---|---|
| 1,822,330 A | 9/1931 | Ainslie |
| 2,748,773 A | 6/1956 | Vacheresse |

(Continued)

FOREIGN PATENT DOCUMENTS

| | | |
|---|---|---|
| DE | 4235602 A1 | 4/1994 |
| DE | 4334746 A1 | 4/1995 |

(Continued)

OTHER PUBLICATIONS

Arthrotek, BiPass Suture Punch, 2006, 6 pages.
International Search Report for Application No. PCT/US2017/016854 dated Apr. 17, 2017.

*Primary Examiner* — Gregory A Anderson
(74) *Attorney, Agent, or Firm* — Lerner, David, Littenberg, Krumholz & Mentlik, LLP

(57) ABSTRACT

An apparatus for passing one or more sutures in tissue repair and/or other surgical procedures. The apparatus includes a pair of jaws mounted on a distal end of a shaft, a hand assembly mounted on a proximal end of the shaft, and a curved needle mounted on the hand assembly and through a shaft. The curved needle remains within the jaw assembly and can be actuated out of the jaw assembly without deformation of the needle and by linear advancement of a needle linkage.

20 Claims, 12 Drawing Sheets

Related U.S. Application Data continuation of application No. 15/072,243, filed on Mar. 16, 2016, now Pat. No. 9,439,647.

(60) Provisional application No. 62/302,190, filed on Mar. 2, 2016.

(52) U.S. Cl.
CPC ..... *A61B 17/06066* (2013.01); *A61B 2017/0608* (2013.01); *A61B 2017/06009* (2013.01); *A61B 2017/06042* (2013.01); *A61B 2017/2925* (2013.01); *A61B 2017/2946* (2013.01)

(56) References Cited

U.S. PATENT DOCUMENTS

| | | | |
|---|---|---|---|
| 3,470,875 A | 10/1969 | Johnson | |
| 3,807,407 A | 4/1974 | Schweizer | |
| 3,842,840 A | 10/1974 | Schweizer | |
| 3,901,244 A | 8/1975 | Schweizer | |
| 3,946,740 A | 3/1976 | Bassett | |
| 4,569,131 A | 2/1986 | Falk et al. | |
| 4,890,615 A | 1/1990 | Caspari et al. | |
| 4,923,461 A | 5/1990 | Caspari et al. | |
| 4,957,498 A | 9/1990 | Caspari et al. | |
| 5,176,702 A | 1/1993 | Bales et al. | |
| 5,254,126 A | 10/1993 | Filipi et al. | |
| 5,312,422 A | 5/1994 | Trott | |
| 5,314,424 A | 5/1994 | Nicholas | |
| 5,387,227 A | 2/1995 | Grice | |
| 5,391,174 A | 2/1995 | Weston | |
| 5,425,743 A | 6/1995 | Nicholas | |
| 5,431,666 A | 7/1995 | Sauer et al. | |
| 5,437,681 A * | 8/1995 | Meade ............ A61B 17/0469 606/139 |
| 5,454,823 A | 10/1995 | Richardson et al. | |
| 5,474,565 A | 12/1995 | Trott | |
| 5,483,952 A | 1/1996 | Aranyi | |
| 5,499,998 A | 3/1996 | Meade | |
| 5,522,820 A | 6/1996 | Caspari et al. | |
| 5,613,977 A | 3/1997 | Weber et al. | |
| 5,626,608 A | 5/1997 | Cuny et al. | |
| 5,676,675 A | 10/1997 | Grice | |
| 5,690,653 A | 11/1997 | Richardson et al. | |
| 5,730,747 A | 3/1998 | Ek et al. | |
| 5,814,054 A | 9/1998 | Kortenbach et al. | |
| 5,824,009 A | 10/1998 | Fukuda et al. | |
| 5,980,538 A | 11/1999 | Fuchs et al. | |
| 6,077,286 A | 6/2000 | Cuschieri et al. | |
| 6,117,158 A | 9/2000 | Measamer et al. | |
| 6,245,079 B1 | 6/2001 | Nobles et al. | |
| 6,299,624 B1 | 10/2001 | Cuschieri et al. | |
| 6,511,487 B1 | 1/2003 | Oren et al. | |
| 6,527,785 B2 | 3/2003 | Sancoff et al. | |
| 6,533,795 B1 | 3/2003 | Tran et al. | |
| 6,638,283 B2 | 10/2003 | Thal | |
| 6,770,084 B1 | 8/2004 | Bain et al. | |
| 6,896,686 B2 | 5/2005 | Weber | |
| 6,916,332 B2 | 7/2005 | Adams | |
| 6,921,408 B2 | 7/2005 | Sauer | |
| 6,984,237 B2 | 1/2006 | Hatch et al. | |
| 7,004,951 B2 | 2/2006 | Gibbens, III | |
| 7,011,668 B2 | 3/2006 | Sancoff et al. | |
| 7,037,315 B2 | 5/2006 | Sancoff et al. | |
| D523,554 S | 6/2006 | Weisel | |
| 7,063,715 B2 | 6/2006 | Onuki et al. | |
| D529,173 S | 9/2006 | Weisel | |
| 7,112,208 B2 | 9/2006 | Morris et al. | |
| D530,421 S | 10/2006 | Topper et al. | |
| 7,131,978 B2 | 11/2006 | Sancoff et al. | |
| 7,131,979 B2 | 11/2006 | DiCarlo et al. | |
| 7,131,980 B1 | 11/2006 | Field et al. | |
| 7,166,116 B2 | 1/2007 | Lizardi et al. | |
| 7,232,448 B2 | 6/2007 | Battles et al. | |
| 7,338,513 B2 | 3/2008 | Lee et al. | |
| 7,377,926 B2 | 5/2008 | Topper et al. | |
| 7,381,212 B2 | 6/2008 | Topper et al. | |
| 7,407,505 B2 | 8/2008 | Sauer et al. | |
| 7,431,188 B1 | 10/2008 | Marczyk | |
| 7,458,966 B2 | 12/2008 | Frank et al. | |
| 7,543,730 B1 | 6/2009 | Marczyk | |
| 7,565,993 B2 | 7/2009 | Milliman et al. | |
| 7,572,265 B2 | 8/2009 | Stone et al. | |
| 7,585,305 B2 | 9/2009 | Dreyfuss | |
| 7,727,256 B2 | 6/2010 | McGregor | |
| 7,879,046 B2 | 2/2011 | Weinert et al. | |
| 7,879,048 B2 | 2/2011 | Bain et al. | |
| 7,922,744 B2 | 4/2011 | Morris et al. | |
| 7,935,128 B2 | 5/2011 | Rioux et al. | |
| 7,938,839 B2 | 5/2011 | DiFrancesco et al. | |
| 7,972,344 B2 | 7/2011 | Murray et al. | |
| 8,123,764 B2 | 2/2012 | Meade et al. | |
| 8,177,796 B2 | 5/2012 | Akyuz et al. | |
| 8,460,318 B2 | 6/2013 | Murray et al. | |
| 8,821,518 B2 | 9/2014 | Saliman et al. | |
| 8,920,441 B2 | 12/2014 | Saliman | |
| 9,173,655 B2 | 11/2015 | Martin | |
| 2002/0065526 A1 | 5/2002 | Oren et al. | |
| 2002/0103493 A1 | 8/2002 | Thal | |
| 2002/0138084 A1 | 9/2002 | Weber | |
| 2002/0147456 A1 | 10/2002 | Diduch et al. | |
| 2003/0083695 A1 | 5/2003 | Morris et al. | |
| 2003/0220657 A1 | 11/2003 | Adams | |
| 2003/0220659 A1 | 11/2003 | Schmieding et al. | |
| 2003/0233106 A1 | 12/2003 | Dreyfuss | |
| 2004/0010273 A1 | 1/2004 | Diduch et al. | |
| 2004/0015177 A1 | 1/2004 | Chu | |
| 2004/0249394 A1 | 12/2004 | Morris et al. | |
| 2004/0260314 A1 | 12/2004 | Lizardi et al. | |
| 2005/0043748 A1 | 2/2005 | Oren et al. | |
| 2005/0085832 A1 | 4/2005 | Sancoff et al. | |
| 2005/0222597 A1 | 10/2005 | Frank et al. | |
| 2005/0234479 A1 | 10/2005 | Hatch et al. | |
| 2005/0245932 A1 | 11/2005 | Fanton et al. | |
| 2005/0288690 A1 | 12/2005 | Bourque et al. | |
| 2006/0020273 A1 | 1/2006 | Hatch et al. | |
| 2006/0190016 A1 | 8/2006 | Onuki et al. | |
| 2006/0271073 A1 | 11/2006 | Lam et al. | |
| 2006/0271074 A1 | 11/2006 | Ewers et al. | |
| 2006/0282098 A1 | 12/2006 | Shelton et al. | |
| 2007/0016248 A1 | 1/2007 | Cuschieri et al. | |
| 2007/0060953 A1 | 3/2007 | Morris et al. | |
| 2007/0123914 A1 | 5/2007 | Lizardi et al. | |
| 2007/0149986 A1 | 6/2007 | Morris et al. | |
| 2007/0225735 A1 | 9/2007 | Stone et al. | |
| 2007/0255317 A1 | 11/2007 | Fanton et al. | |
| 2007/0260259 A1 | 11/2007 | Fanton et al. | |
| 2007/0270885 A1 | 11/2007 | Weinert et al. | |
| 2008/0027468 A1 | 1/2008 | Fenton et al. | |
| 2008/0208221 A1 | 8/2008 | Murray et al. | |
| 2008/0255588 A1 | 10/2008 | Hinman | |
| 2008/0275469 A1 | 11/2008 | Fanton et al. | |
| 2008/0312669 A1 | 12/2008 | Vries et al. | |
| 2009/0062816 A1 | 3/2009 | Weber | |
| 2009/0062819 A1 | 3/2009 | Burkhart et al. | |
| 2009/0088781 A1 | 4/2009 | Prestel et al. | |
| 2009/0131956 A1 | 5/2009 | Dewey et al. | |
| 2009/0177039 A1 | 7/2009 | Frank | |
| 2010/0121352 A1 | 5/2010 | Murray et al. | |
| 2010/0152751 A1 | 6/2010 | Meade et al. | |
| 2010/0256656 A1 | 10/2010 | Park | |
| 2011/0060350 A1 | 3/2011 | Powers et al. | |
| 2011/0087245 A1 | 4/2011 | Weinert et al. | |
| 2011/0118760 A1 | 5/2011 | Gregoire et al. | |
| 2011/0152891 A1 | 6/2011 | McLawhorn et al. | |
| 2011/0251626 A1 | 10/2011 | Wyman et al. | |
| 2012/0116422 A1 | 5/2012 | Triplett et al. | |
| 2012/0277767 A1 | 11/2012 | Powers et al. | |
| 2013/0030450 A1 | 1/2013 | Dreyfuss et al. | |
| 2014/0236193 A1 | 8/2014 | Chin et al. | |

FOREIGN PATENT DOCUMENTS

| | | | |
|---|---|---|---|
| EP | 0812572 B1 | 8/2003 | |
| EP | 1067872 B1 | 3/2006 | |

(56) References Cited

FOREIGN PATENT DOCUMENTS

| | | | |
|---|---|---|---|
| EP | 1498075 | B1 | 8/2009 |
| WO | 9639948 | A | 12/1996 |
| WO | 9710756 | A | 3/1997 |

* cited by examiner

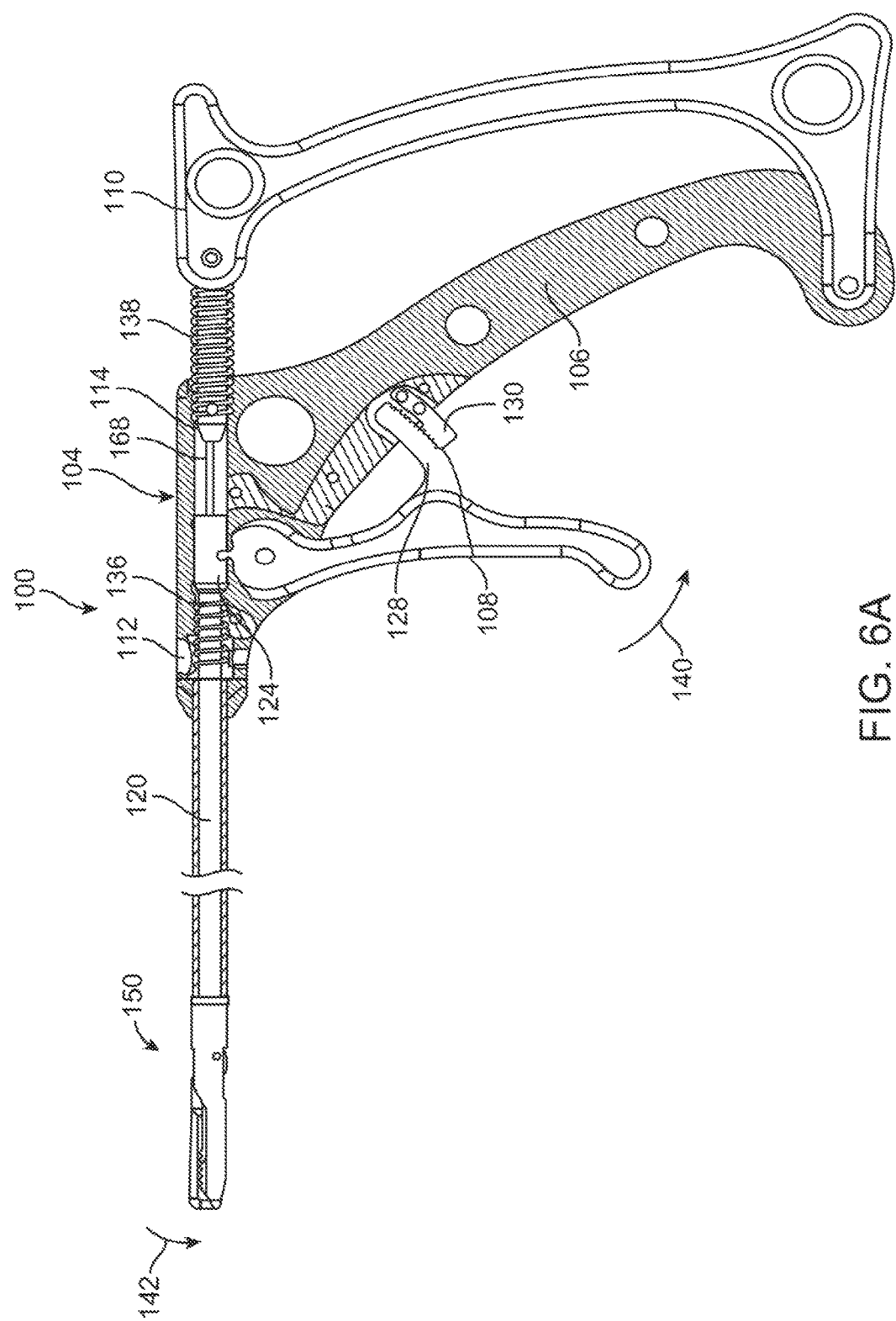

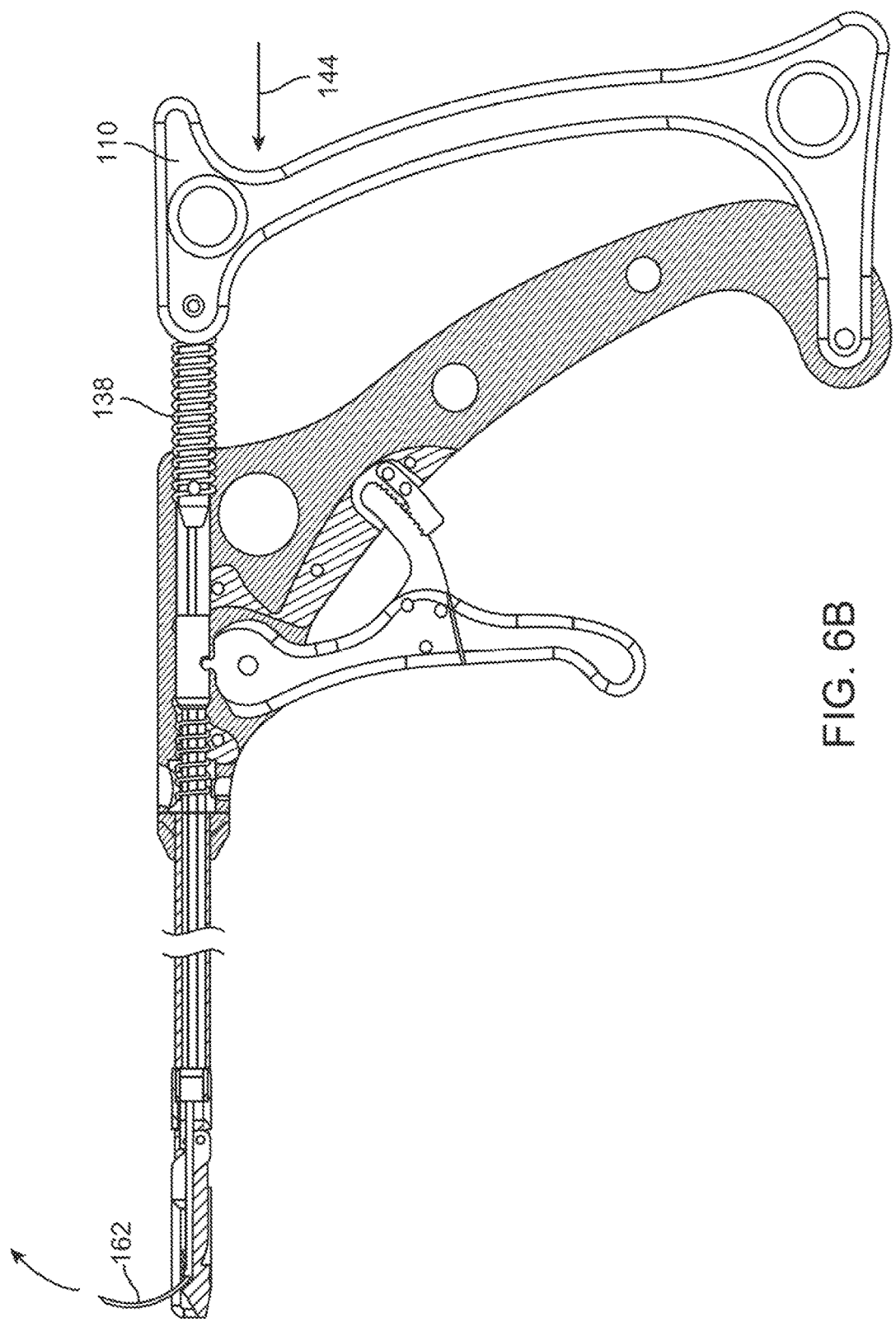

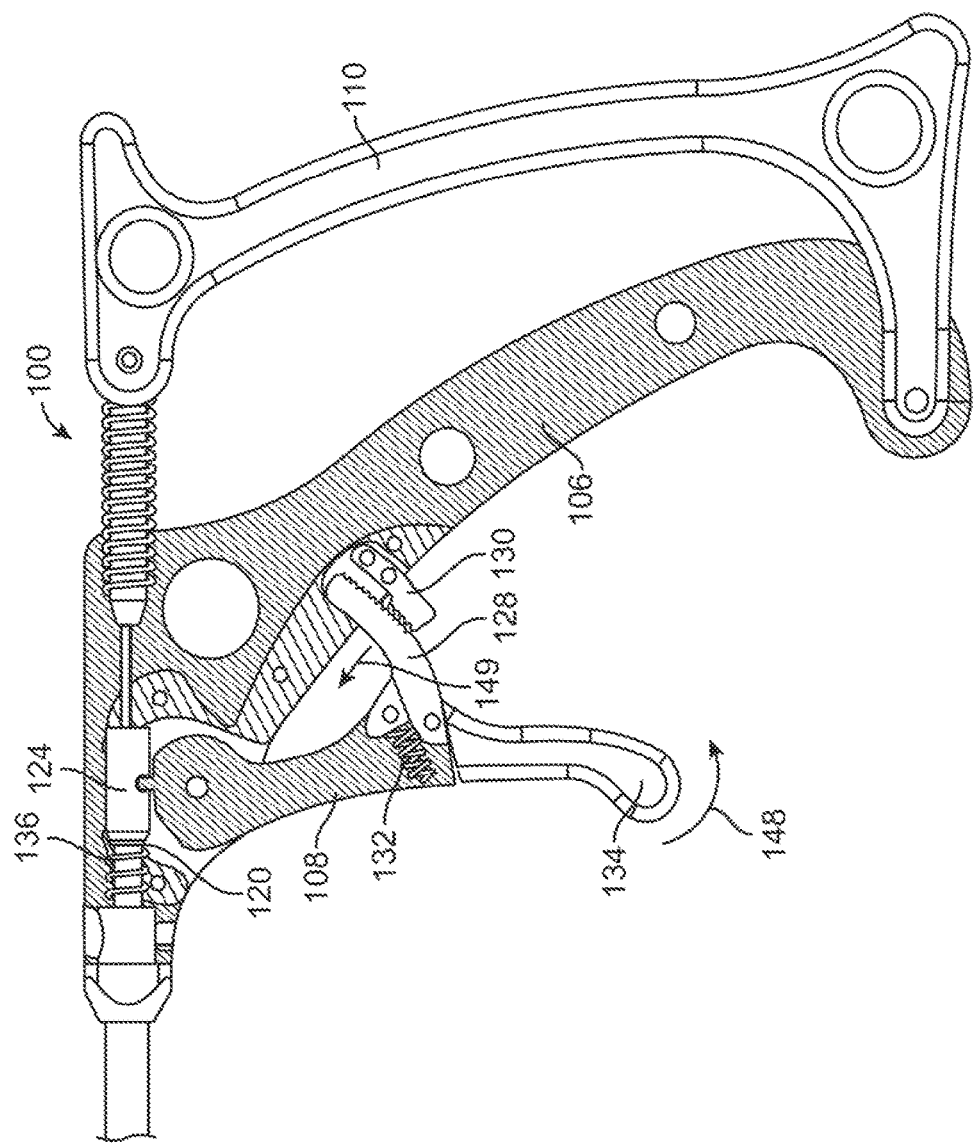

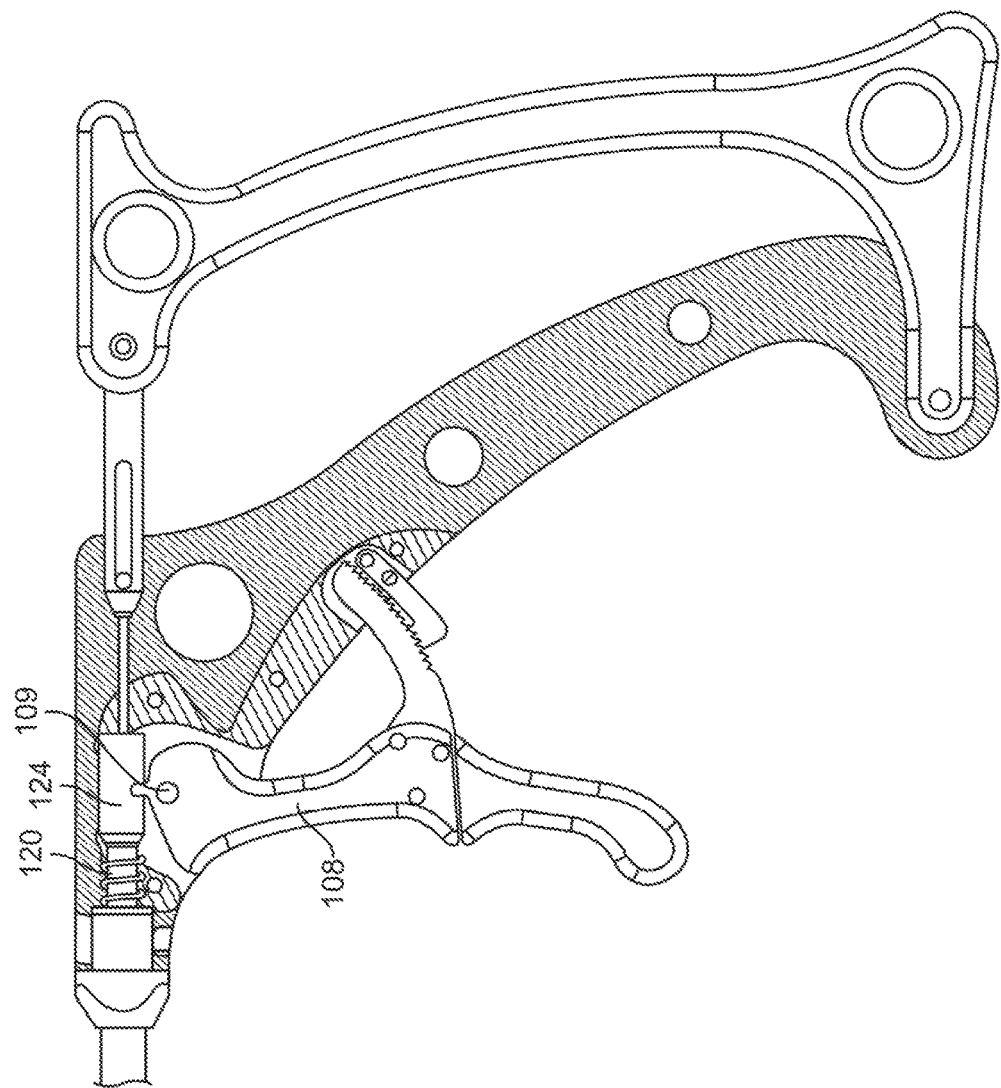

SUTURE PASSING INSTRUMENTS AND METHODS

RELATED APPLICATIONS

This application is a continuation of U.S. patent application Ser. No. 15/261,521 filed Sep. 9, 2016, which is a continuation of U.S. patent application Ser. No. 15/072,243 filed Mar. 16, 2016 (now U.S. Pat. No. 9,439,647 issued Sep. 13, 2016), which is a non-provisional of U.S. Provisional Application No. 62/302,190 filed Mar. 2, 2016, the entirety of which is incorporated by reference.

FIELD OF THE INVENTION

The present invention includes surgical instruments that are configured to secure tissue and pass a needle through the secured tissue where the needle is equipped to deliver a suture through the tissue. Typically such suture passing instruments are used for tissue repair procedures.

BACKGROUND

Suturing devices are commonly used for open and endoscopic surgical procedures that require the use of a suture to ligate, join, re-attach tendon to bone, or otherwise secure adjoining tissue. Many such suturing devices grasp the tissue with a jaw assembly and pass the suture through the tissue using a needle that undergoes deformation either when loaded into the device, or upon exiting the device. Many of these devices rely on super-elastic needles that must be replaced.

However, the use of needles that undergo deformation can present problems in that the needles often fail by breaking and must be replaced. On many occasions, the needle fails during the surgical procedure and must be removed from inside a patient, which causes added difficulty, time and cost to the procedure. The cost of replacement needles, especially those fabricated from a superplastic material, can be excessive.

Accordingly, there is a need for a suture passing instrument that may be operated in the manner similar to conventional suture passing devices but employ a pre-curved needle that does not experience deformation within the suturing device or during deployment of the suturing device. Elimination of the deformation of the needle can allow for a device with a fixed needle, that can optionally be reusable, which can result in a cost savings.

In view of the above, there remains a need to provide an improved suture passing device.

SUMMARY OF THE INVENTION

The illustrations and variations described herein are meant to provide examples of the methods and devices of the invention. It is contemplated that combinations of aspects of specific embodiments or combinations of the specific embodiments themselves are within the scope of this disclosure.

The present disclosure includes suture passing instruments having a curved needle that does not experience deformation within the suture passing device and during deployment. Such a suturing device can provide a fixed needle rather than a disposable or replaceable needle.

In one example the suture passing device comprises a shaft having a far portion and a near portion; a handle assembly located at the near end of the shaft and comprising a needle actuator moveably coupled to a handle portion, a trigger lever moveably coupled to the handle portion, the handle portion coupled to the near end of the shaft; a jaw assembly comprising an actuating jaw moveably coupled to a fixed jaw, the fixed jaw located at the far portion of the shaft, where actuation of the trigger lever moves the actuating jaw relative to the fixed jaw to open and close the jaw assembly; a curved needle nested within the fixed jaw and slidable within a curved track of the fixed jaw, where a curvature of the curved needle and a curvature of the track are matched to permit movement of the curved needle through the curved track in without being deformed, the curved needle having a suture carrying slot at a distal portion allowing for loading of a suture external to the shaft; and a needle linkage having a first end coupled to a proximal section of the curved needle at a pivot joint and a second end coupled to the needle actuator, such that movement of the needle actuator advances the needle linkage in a forward direction to move the curved needle through the curved track and out through a top of the jaw assembly without deformation of the curved needle, where the pivot joint permits axial movement of the needle linkage without deformation.

The suture passing device can also include a variation the fixed jaw comprises an opening at a distal end exposing the suture carrying slot for loading of the suture external to the shaft. This slot may be through the center or side of the lower fixed jaw.

In another example, the suture passing device of can comprise an actuating jaw having an opening at a distal end to further expose the suture carrying slot when the jaw assembly is closed.

In another variation, the suture passing device further comprises a jaw linkage located within the shaft and having a first end and a second end, the first end of the jaw linkage engaged with the actuating jaw, the second end of the jaw linkage engaged with the trigger lever, such that movement of the trigger lever relative to the handle portion causes movement of the jaw linkage causing movement of the actuating jaw relative to the fixed jaw.

Variations of the suture passing device can include a trigger lever that comprises a first actuator portion pivotally coupled to the handle portion and a second locking portion pivotally coupled to the first actuator portion, where the second locking portion comprises a trigger locking surface moveably engaged with a handle locking surface, such that when engaged, the trigger locking surface and handle locking surface locks the trigger lever in place to lock the jaw assembly in place.

In an additional variation, the suture passing device can include a second locking portion that is spring biased against the first actuator portion, and where relative movement between the first actuator portion and the second locking portion causes disengagement of the trigger locking surface from the handle locking surface to release the jaw assembly. In additional variations, the device can be used with or without a ratchet lock configuration.

In an additional variation, the pivot joint comprises a bore in the proximal section of the curved needle and a slot in the first end of the needle linkage. Alternatively, variations of the device can comprise a curved needle and needle linkage that are continuous and the pivot joint comprises a living hinge between the curved needle and needle linkage.

In another variation, the suture passing device described herein can include a needle actuator that is spring biased against the handle portion to cause the curved needle to remain within the curved track until a force is applied to the needle actuator. Variations of the device can also include a locking mechanism to prevent motion of the needle in the locked position.

In additional variations, the trigger lever can be spring biased against the handle portion to cause the jaw assembly to remain open until a force is applied to the trigger lever.

Variations of the suture passing devices include a needle actuator that is moveably coupled to the handle portion at an end of the handle portion opposite to the shaft.

BRIEF DESCRIPTION OF THE DRAWINGS

Each of the following figures diagrammatically illustrates aspects and variation to better understand the invention. Variation of the invention from the aspects shown in the figures is contemplated.

FIGS. 6A to 6C illustrate actuation of an example of a handle assembly to drive the suture passing device.

FIGS. 7, 8A, and 8B show alternate variations of suture passing devices.

DETAILED DESCRIPTION THE INVENTION

Figure 1:
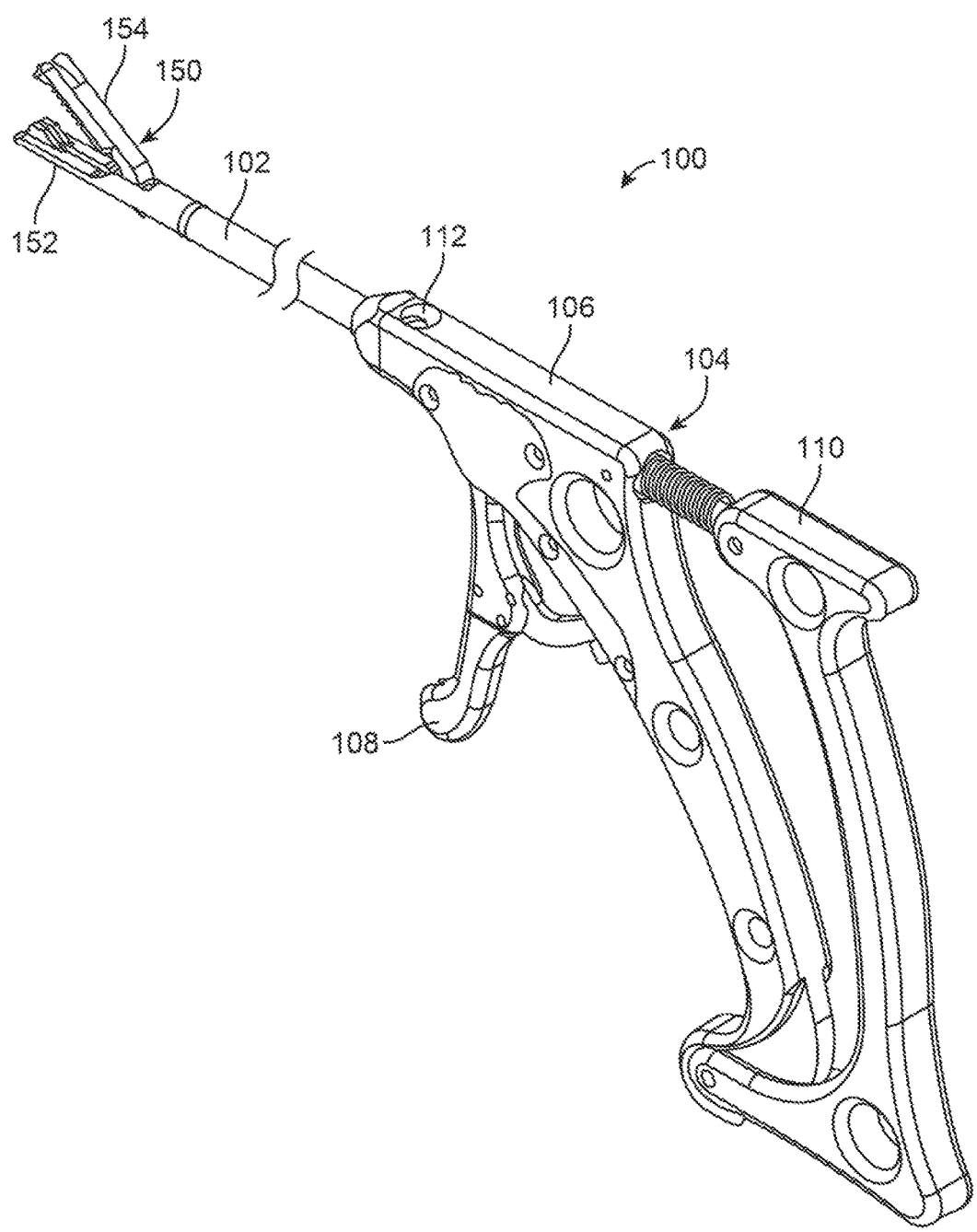
FIG. 1 illustrates an example of a suture passing device having an elongate shaft with a handle assembly located at a near or proximal end of the shaft and a jaw assembly located at a far or distal end of the shaft.

FIG. 1 illustrates a first example of a suture passing device 100 having an elongate shaft 102 with a handle assembly 104 located at a near or proximal end of the shaft 102 and a jaw assembly 150 located at a far or distal end of the shaft 102.

The handle assembly 104 shown in FIG. 1 includes a handle portion 106 that is fixedly attached to the shaft 102. Alternate variations can include rotational coupling between the shaft 102 and handle portion 106. Where such rotational coupling can include ratchetable configuration and/or a freely rotational coupling with or without the ability to lock the two components together. In addition, the handle assembly 104 of the present invention can comprise any handle configuration used with known suture passing devices or related technology. In the illustrated example, the handle portion 106 of the variation shown in FIG. 1 includes a trigger lever 108 moveable relative to the handle portion 106, which actuates the jaw assembly 150. The handle assembly 104 can also include a separate needle actuator 110 that is moveably coupled to the handle portion 106, where movement of the needle actuator 110 drives a needle element as discussed below. The suture passing device 100 can also include a port 112 that aids in cleaning and decontamination of the device. For example, the port 112 can permit fluids to pass through the shaft 102 and through the jaw assembly 150 for cleaning and sterilizing. In additional variations, the shaft can be decoupled from the assembly to permit a thorough cleaning.

Figure 2A:
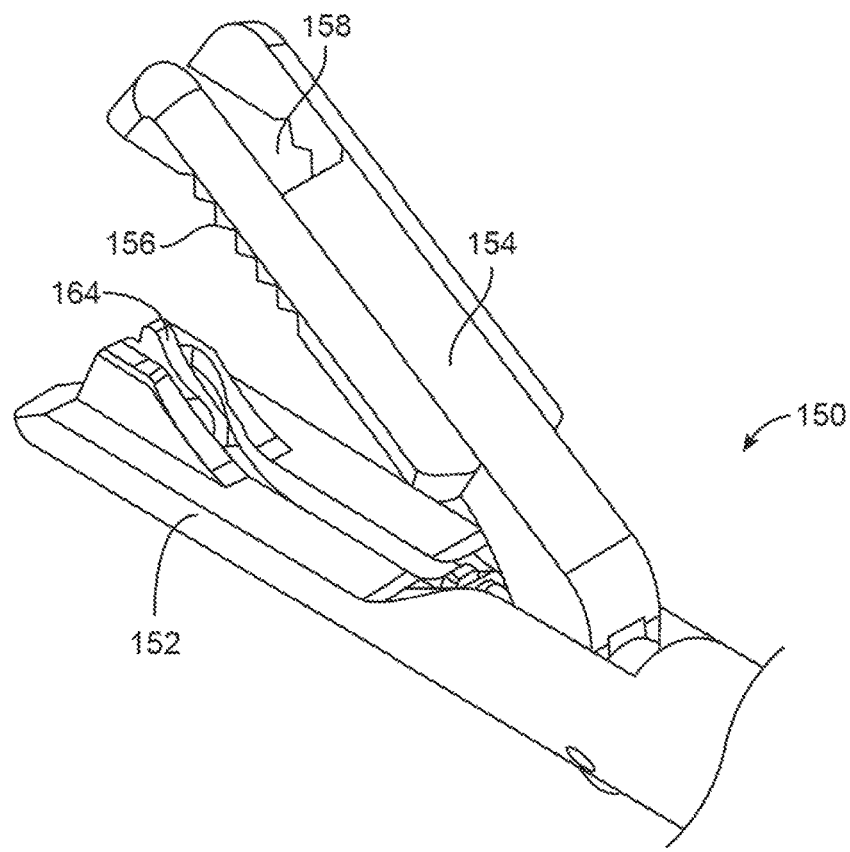
FIG. 2A illustrates a magnified view of the jaw assembly of FIG. 1.

FIG. 1 also shows the jaw assembly 150 comprising a fixed jaw 152 and an actuating jaw 154 that is configured to pivot relative to the fixed jaw 152 to secure tissue therebetween. FIG. 2A illustrates a magnified view of the jaw assembly 150 of FIG. 1 where the jaw assembly 150 is in an open configuration. As shown, the actuating jaw 154 can include a surface 156 configured to close against the fixed jaw 152 to secure tissue therebetween. This surface 156 can include ridges, or other protrusion to improve securing of the tissue.

The actuating jaw 154 also includes a channel 158 that allows for delivery of the needle and suture (not shown in FIG. 2A) through the clamped jaw assembly 150. The channel 158 is positioned in line with a track 164 of the lower or fixed jaw 152 so as to not impede movement of the suture and needle when the needle is actuated.

Figure 2B:
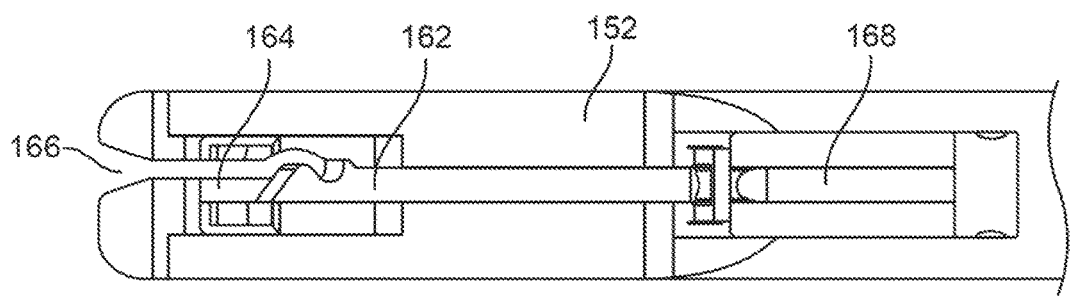
FIG. 2B illustrates a top view of the fixed jaw (where the upper or actuating jaw is omitted for purposes of illustration).

FIG. 2B illustrates a top view of the fixed jaw 152 (where the upper or actuating jaw is omitted for purposes of illustration). As shown in FIG. 2B, a needle 162 is nested within a track 164 of the fixed jaw 152. The needle 162 comprises a curved shape (as discussed below) and is coupled to a needle linkage 168. Where the opposite end of the needle linkage 168 couples to an actuator on the handle portion (not shown).

Figure 2C:
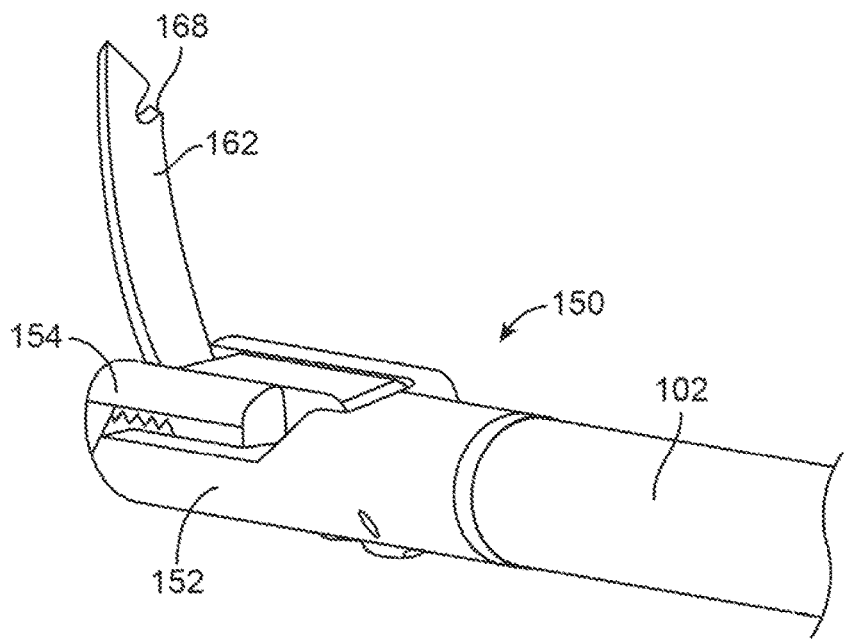
FIG. 2C illustrates a needle extending from the jaw assembly in an actuated position when the actuating jaw is clamped against the fixed jaw at the end of the shaft.
Figure 2D:
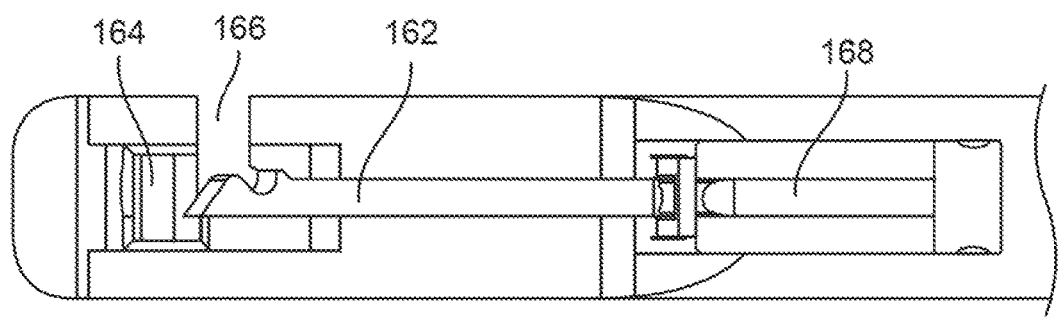
FIG. 2D illustrates a top view of the fixed jaw with a side opening to load a suture (where the upper or actuating jaw is omitted for purposes of illustration).

The fixed jaw 152 includes a suture channel 166 that permits loading of the suture onto the needle 162. In the example show in FIG. 2C, the needle 162 includes a suture groove 168 that nests a suture when the suture is advanced through the suture channel 166 onto the needle 162. Alternate variations can include sutures being loaded onto a tip of the needle itself. In alternate variations, the device can allow for side-loading of a suture through a slot in fixed jaw 152 located on a side of the device and as shown in FIG. 2D. FIG. 2C illustrates a needle 162 extending from the jaw assembly 150 in an actuated position when the actuating jaw 154 is clamped against the fixed jaw 152 at the end of the shaft 102. As shown, this example of the device includes a needle 162 comprising a flat construction. However, additional variations of the devices can include needles having other cross-sectional geometries (e.g., circular, oval, hollow, triangular, etc.).

Figure 3A:
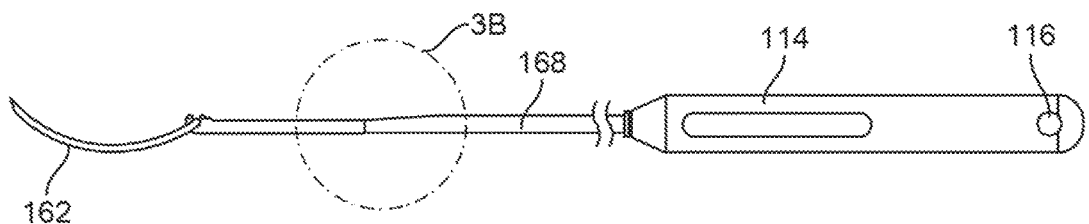
FIG. 3A shows an example of a needle coupled to a needle linkage at a first end of the needle linkage and second end of the linkage coupled to a portion of the handle assembly.
Figure 3B:
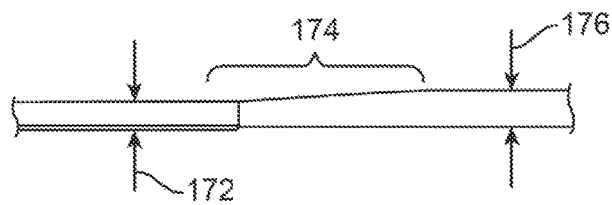
FIG. 3B illustrates a magnified section 3B of FIG. 3A.

FIG. 3A shows an example of a needle 162 coupled to a needle linkage 168 at a first end of the needle linkage 168 and second end of the linkage 168 coupled to a portion 114 of the handle assembly 104. In alternate variations of the device, the needle linkage 168 can be directly coupled to the needle actuator of the handle assembly. However, in the illustrated variation, the coupling portion 114 of the handle assembly is pivotally affixed to the needle actuator (not shown) via a pivot connection at location 116. In addition, a spring (shown in FIG. 1) can be affixed to (or over) the coupling portion 114 to bias the needle in a retracted position (as discussed below). FIG. 3B illustrates a magnified section 3B of FIG. 3A to illustrate that the needle linkage 168 can include one or more features to allow axial translation of the needle actuator to drive the needle linkage 168 within the shaft 102 to actuate the needle 162 from the jaw assembly. In this variation, the needle linkage 168 comprises a tapered portion 174 joining a narrow distal region 172 of the linkage 168 to a larger proximal region 176. As discussed below, this tapered portion 174 allows for the needle linkage 168 to move within the device without interfering with other components of the device.

Figure 3C:
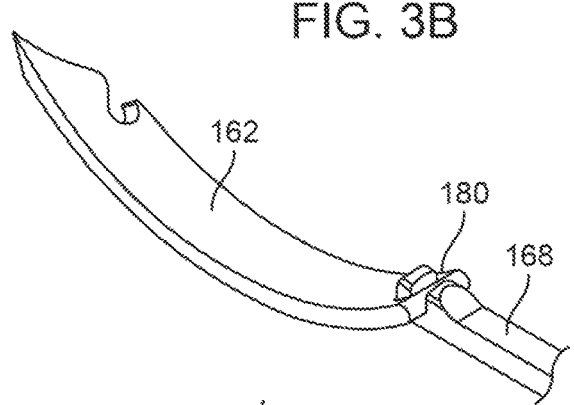
FIG. 3C illustrates the needle coupled to the needle linkage at a pivot joint.

FIG. 3C illustrates the needle 162 coupled to the needle linkage 168 at a pivot joint 180. The pivot joint 180 illustrated is one example of a joint that joins two separate components, a needle 162 and the needle linkage 168. While the illustrated variation shows the needle a member that rests within a slot of the needle linkage, alternate variations of the device can include any number of configurations that couple two separate components. Such a configuration allows the needle to be fabricated from a preferred material, such as an alloy or stainless steel. As discussed herein, the needle 162 comprises a curved configuration that nests within a track having a matching curved configuration therefore there is no deformation of the needle and/or the needle linkage. This permits variations of the suture passing device to include a needle fabricated from a non-shape memory material where the pre-curved needle resides within the suture passing device and does not experience material fatigue from repeated deformation. Such a construction allows for a permanent needle within the suture passing device as opposed to a disposable needle.

As noted above, a variation of the device includes a non-deformable, high strength, and/or rigid needle fabricated from a hardened material. Since the needle is pre-curved and does not undergo deformation when in the device, the hardened needle can be driven through thick, fibrous, calcified, or other difficult tissue that would cause deformation of the conventional type of needles (such as shape memory or Nitinol materials) that are often used in suture passing devices. In one example, the needle material comprises a hardened stainless steel alloy with a UTS (ultimate tensile strength of 230,000 PSI. In such a case, the stainless steel is handed and then is shaped through an electrical discharge machining (EDM) process that cuts or forms the hardened material into a naturally curved state that remains in a permanently non-deformed curved state. This material, combined with a larger cross sectional surface (such as the rectangular cross-sectional profile shown in the figures) provides the ability of the device to apply significant force to the needle when compared to conventional deformable needles (e.g., Nitinol needles). In one example, the pre-curved needle was fabricated from a custom 455 ® Stainless steel with a hardness of H900 provided by Carpenter Technology Corporation (PA).

Figure 3D:
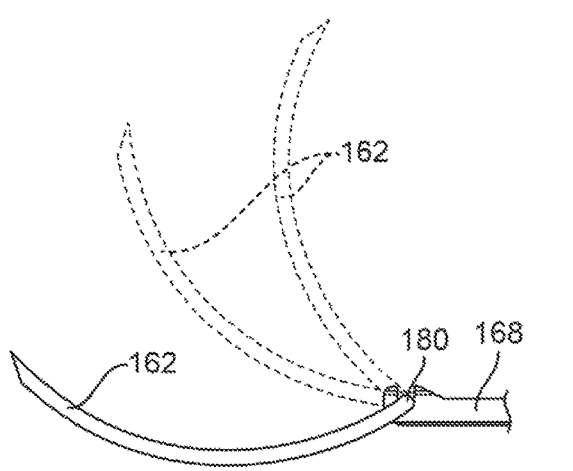
FIG. 3D illustrates a needle freely pivoting relative to a pivot joint.

The pivot joint 180 coupling the needle 162 and the needle linkage 168 allows the needle to freely pivot relative to the needle linkage 168 as shown in FIG. 3D. This rotational movement allows the needle to extend through the track of the slot assembly and through the jaw being advanced by the needle linkage 168, which moves in a linear direction within the device. Although the pivot joint 180 is illustrated to have an open end, variations of the invention can include pivot joints that are closed or covered while allowing the curved needle to pivot relative to the needle linkage 168.

Figure 4A:
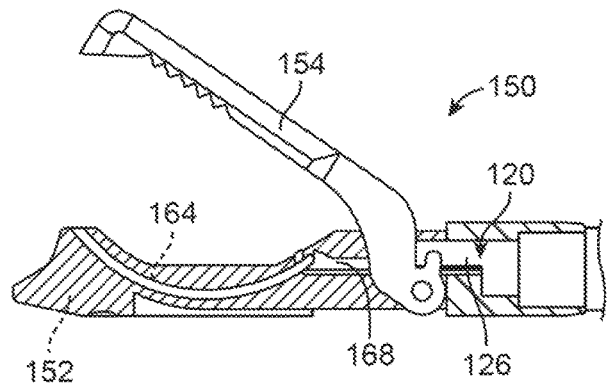
FIG. 4A illustrates a cross sectional view of the jaw assembly in an open position.
Figure 4B:
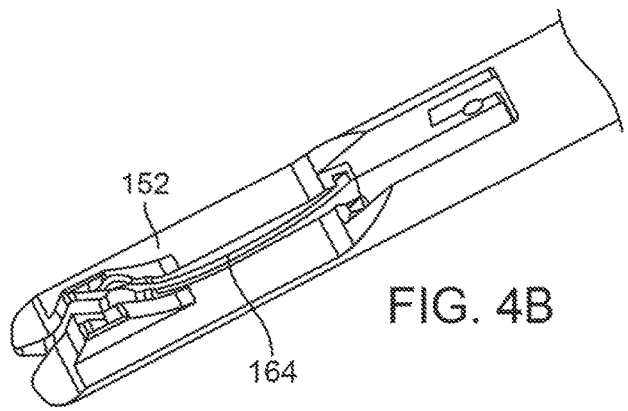
FIG. 4B illustrates the lower jaw without the needle, link member, or upper jaw for purposes of illustrating the needle track.
Figure 4C:
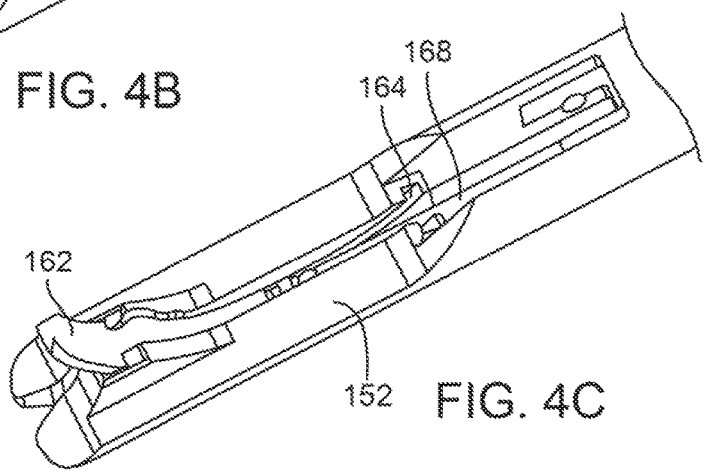
FIG. 4C illustrates the link member advancing a needle partially through the track of the lower jaw.

FIG. 4A illustrates a cross sectional view of the jaw assembly 150 in an open position to illustrate the curved needle track 164 of the fixed jaw 152 to better illustrate the needle track 164 within the fixed jaw 152. In operation, the actuating jaw 154 is driven by a link member 120 that is coupled to a trigger lever (not shown) on the handle assembly. In this variation of the device, the movement of the needle link 168 can occur independently of the actuating jaw linkage 120. For example, as shown, the link member 168 can extend through a passage 122 (see FIG. 4D) of the jaw linkage 120. FIG. 4B illustrates the lower jaw 152 without the needle, link member, or upper jaw for purposes of illustrating the needle track 164. The needle track 164 can allow retention of the needle while permitting unimpeded movement of the link member 168. This movement is illustrated in FIG. 4C where the link member 168 advances a needle 162 partially through the track 164 of the lower jaw 152 and where the track 164 provides clearance for the link member 168 as the pivot joint allows the link member 168 to follow the needle 162 without deformation or entering the track 164.

Figure 4D:
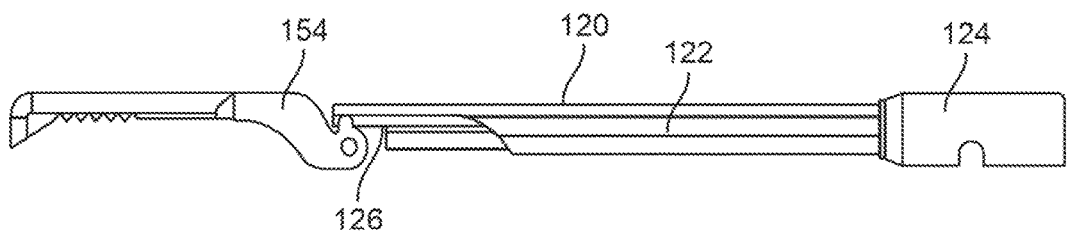
FIG. 4D illustrates a cross section of the articulating jaw and jaw link member to illustrate a passage extending through the jaw link member.

FIG. 4D illustrates a cross section of the articulating jaw 154 and jaw link member 120 to illustrate a passage extending through the jaw link member 120. In the illustrated variation, the passage also extends through a coupling portion 124 on the proximal or near end of the jaw link member 120. The distal or far end of the link member 120 comprises a relief cut 126 that allows the needle link member 168 to follow the needle through the arc of the needle track 164.

FIGS. 5A to 5D illustrate a cross sectional view of the jaw assembly 150 to show the movement of the actuating jaw 154 and needle 162. While the illustrated example shows a fixed lower jaw 152 as containing the needle 162, alternate variations of the device can include both jaws being moveable or just the lower jaw being moveable. Furthermore, in alternate variations of the devices, the curved needle can be positioned in the upper jaw. For purposes of illustration, the actuating jaw 154 is omitted from FIGS. 5C and 5D.

Figure 5A:
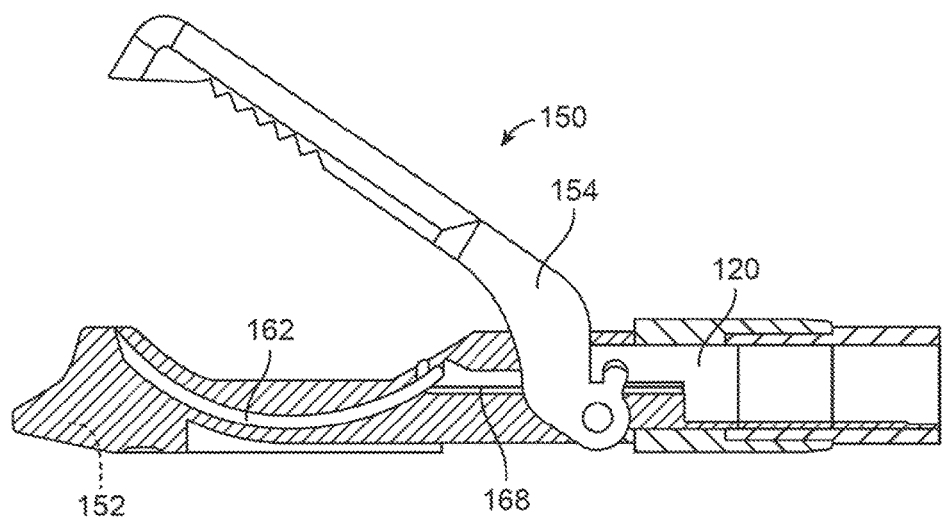
FIGS. 5A to 5D illustrate a cross sectional view of the jaw assembly to show the movement of the actuating jaw and needle.
Figure 5B:
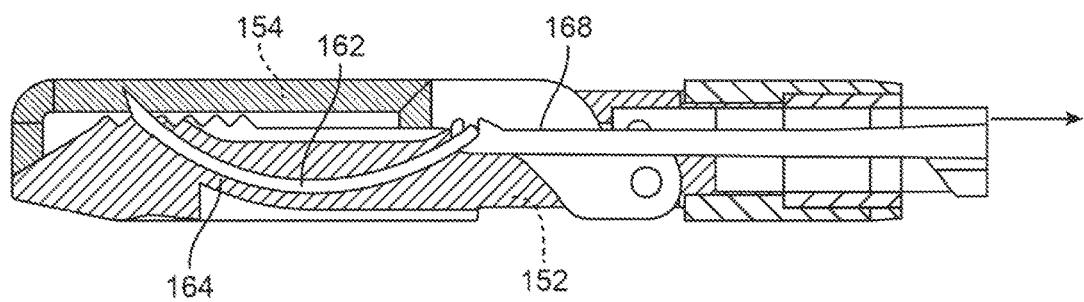
Figure 5C:
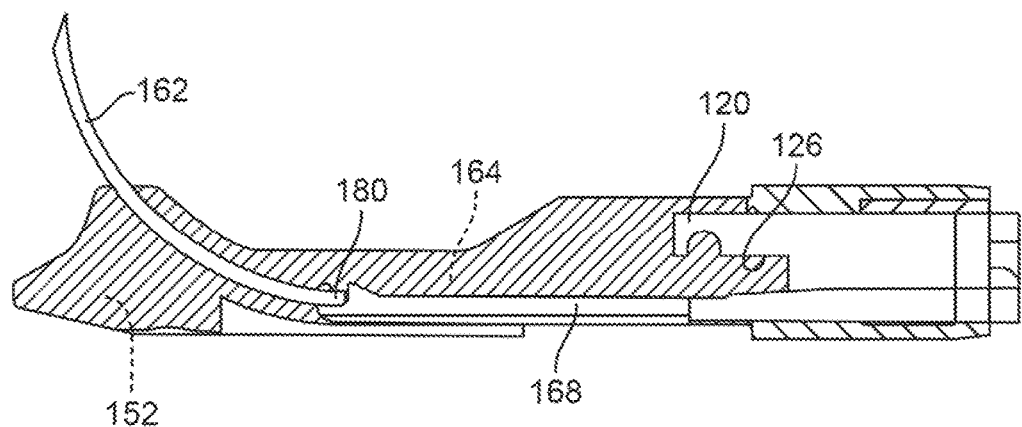
Figure 5D:
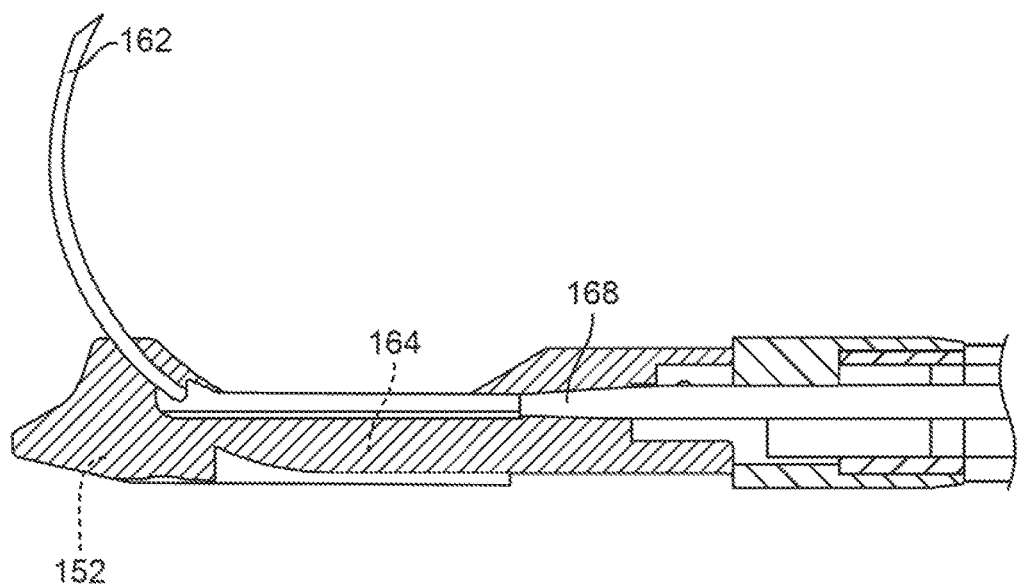

FIG. 5A illustrates a jaw assembly 150 in an open position. Movement of jaw linkage 120 in a distal/far direction causes closure of the actuating jaw 154 against the fixed jaw 152 (as shown in FIG. 5B) without moving the needle linkage 168 or needle 162 that is nested within the needle track in its natural curved state. FIG. 5C illustrates movement of the needle linkage 168 in a distal direction, which drives the needle 162 through the needle track 164 and out of the lower jaw 152. As shown, the pivot joint 180 allows the needle linkage 168 to follow movement of the needle 162 through the track 164 without deforming. Accordingly, the needle linkage 162 moves towards the bottom arc of the needle track 164 due to the relief cut 126 in the jaw linkage 120. FIG. 5D shows the needle link 168 moved in a distal most position to fully advance the needle 162 from the jaw assembly. Again, the needle link 168 moves to follow the arc of the curved needle track 164 and moves towards a top of the lower jaw 152. As shown, the pre-curved needle does not undergo deformation at any point during its movement. The jaw assembly can further include any number of stops on the needle, needle link, and/or jaw to prevent advancement of the needle 162 or needle linkages 168.

FIGS. 6A to 6C illustrate actuation of an example of a handle assembly 104 to drive the suture passing device. The structure shown in these figures is meant to illustrate one possible variation of the inventive suture advancing device. Clearly, any number of handle assemblies is within the scope of this disclosure and claims.

FIG. 6A illustrates a trigger lever 108 that is coupled, indirectly, to a first spring member 136. In this example, the trigger lever 108 engages a coupling portion 124 of the jaw linkage, which carries a first spring 136. The first spring 136 biases the jaw linkage 120 away from the jaw assembly 150 such that the jaw assembly 150 is naturally biased in an open position (as shown in FIG. 1). Likewise, the needle actuator 110 is coupled to a coupling portion 114 of the needle linkage 168 with a second spring member 138 biasing the needle actuator 110 away from the jaw assembly 150 to maintain the needle within the needle track in an initial position.

In some variations of the device 100 the first spring 136 is configured a lower spring constant (or is less stiff) than the second needle spring 138. This balancing of springs allow a user to position the device appropriately and then squeeze the trigger lever 108 while applying force on the needle actuator 110. Because the first spring 136 is less stiff than the second spring 138, the trigger lever 108 pivots at its coupling point and moves in direction 140 to drive the jaw linkage 120 and 124 towards the jaw assembly 150. A variation of the device 100 can include a trigger locking surface 128 that engages a handle 130 locking surface 130 coupled to a handle portion 106. Such surfaces can comprise a ratchet and pawl system or detent system. In the illustrated variation, and as discussed below, the trigger locking surface 128 can be spring biased to remain against the handle locking portion 130 such that movement of trigger in direction 140 is prevented from reversing while the trigger locking surface 128 remains engaged with the handle locking surface 130.

Once the jaws close (as shown in FIG. 6A in direction 142) the jaw linkage 120 and 124 are prevented from moving, which causes any closing force applied to the handle assembly 104 to be directed to the needle actuator 110. This force compresses the second spring 138 to cause movement of the needle actuator 110 in direction 144 causing movement of the needle 162 as shown in FIG. 6B.

FIG. 6C illustrates the device after the needle actuator 110 returns to the normal position where the needle is seated within the needle track and after the suturing procedure is completed. This variation of the device 100 includes a two part trigger lever. A first part 108 of the trigger lever actuates the jaw assembly as described above. The second part 134 of the trigger assembly is spring biased by trigger spring 132 to maintain trigger locking surface 128 in engagement with the handle 130 locking surface 130. To release the two surfaces 128, 130, the operator moves the second part 134 of the trigger lever to compress the trigger spring 132. This compression causes movement of the trigger locking surface 128 away from the handle locking surface 130 in direction 149. The disengagement of the locking surfaces 128 and 130 (and release of trigger 108 by operator) allows the jaw spring 136 to move the jaw linkage 120 and coupling portion 124 away from clamp assembly 150 causing the jaw assembly to open.

FIG. 7 illustrates another variation of a suture passing device as discussed above. In this variation, the trigger lever 108 that drives the jaw assembly is configured to increase a clamping force of the jaw assembly (not shown in FIG. 7). In this variation, the pivot 109 of the trigger lever 108 is moved closer to the coupling portion 124 of the jaw linkage 120. This permits the user to apply an increased force to close the jaw assembly, which may be necessary when driving a rigid curved needle through fibrous or other hardened tissue material.

Figure 8A:
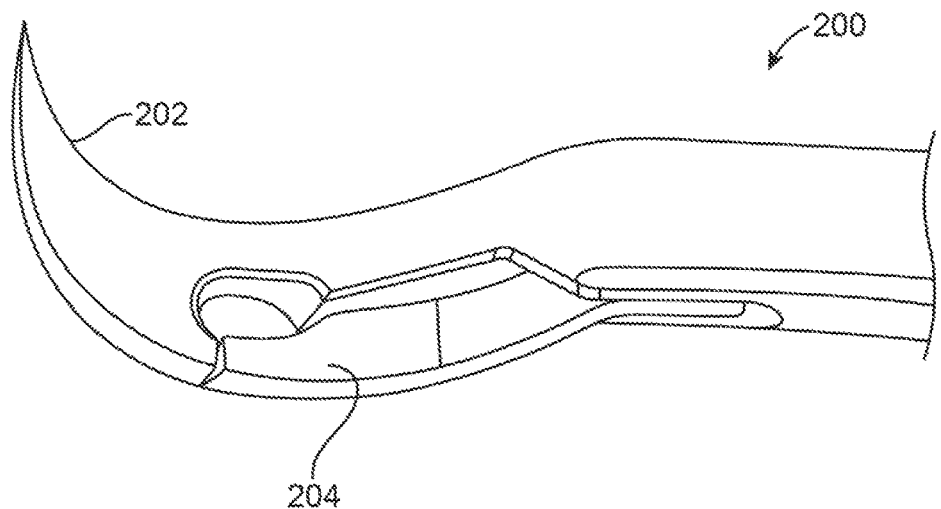
Figure 8B:
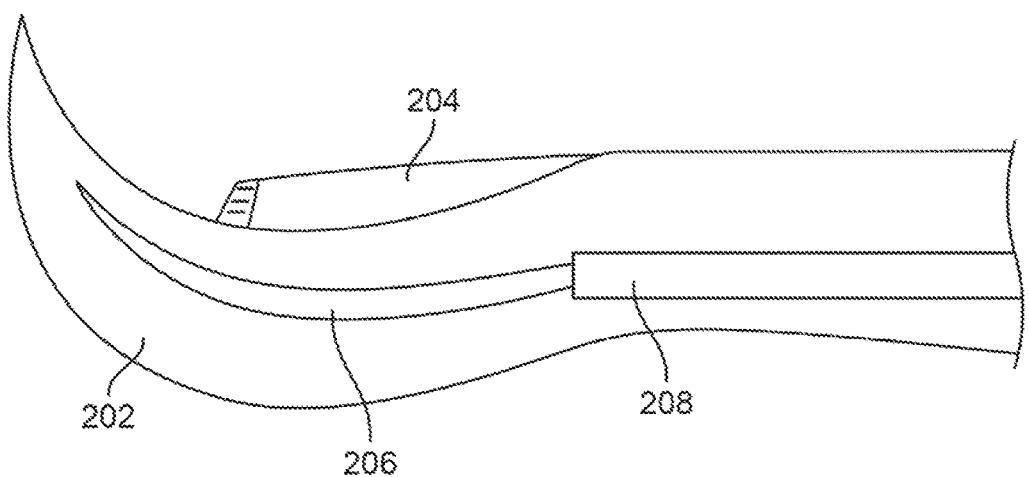

FIGS. 8A and 8B represent additional variations of jaw structures for use with the concepts disclosed herein. FIG. 8A illustrates a device 200 useful for glenoid repair procedures in which the fixed jaw 202 comprises a curved sharp tip adjacent to a grasping jaw 204. FIG. 8B illustrates a cross sectional view of a similar device where a curved needle 206 and linkage 208 reside within the curved jaw 202.

A number of embodiments of the invention have been described. Nevertheless, it will be understood that various modifications may be made without departing from the spirit and scope of the invention. Combination of the aspect of the variations discussed above as well combinations of the variations themselves are intended to be within the scope of this disclosure.

Various changes may be made to the invention described and equivalents (whether recited herein or not included for the sake of some brevity) may be substituted without departing from the true spirit and scope of the invention. Also, any optional feature of the inventive variations may be set forth and claimed independently, or in combination with any one or more of the features described herein. Accordingly, the invention contemplates combinations of various aspects of the embodiments or combinations of the embodiments themselves, where possible. Reference to a singular item, includes the possibility that there are plural of the same items present. More specifically, as used herein and in the appended claims, the singular forms "a," "and," "said," and "the" include plural references unless the context clearly dictates otherwise.

What is claimed is:

1. A surgical device comprising:
a shaft having a proximal end and a distal end;
a handle assembly including a first actuator and a second actuator each moveably coupled to a handle portion that is coupled to the proximal end of the shaft;
a jaw assembly located at the distal end of the shaft and including a fixed jaw defining a curved needle track and an actuating jaw moveably coupled to the fixed jaw, wherein the second actuator is configured to move the actuating jaw relative to the fixed jaw;
a curved needle slidable within the curved needle track, wherein the curved needle track is defined by curved top and bottom surfaces that substantially match a curvature of the curved needle; and
a third actuator coupled to the first actuator and to a proximal portion of the curved needle,
wherein a coupling between the third actuator and the proximal portion of the curved needle allows the first actuator to move the curved needle via the third actuator without deforming the curved needle.

2. The surgical device of claim 1, wherein the coupling between the third actuator and the proximal portion of the curved needle is a pivot joint.

3. The surgical device of claim 1, wherein the coupling between the third actuator and the proximal portion of the curved needle permits proximal-distal movement and superior-inferior movement of a distal end of the third actuator.

4. The surgical device of claim 1, wherein the substantially matched curvatures of the curved needle and the curved needle track permit movement of the curved needle through the curved track without deformation of the curved needle.

5. The surgical device of claim 1, wherein the third actuator includes a wider proximal region that tapers to a narrower distal region.

6. The surgical device of claim 1, wherein the distal end of the third actuator travels along a curvature of the curved needle track during actuation of the third actuator.

7. The surgical device of claim 1, where the fixed jaw includes an opening at a distal portion thereof exposing a suture carrying slot of the curved needle such that a suture can be loaded outside the shaft.

8. The surgical device of claim 7, wherein the opening has a mouth at a side surface of the fixed jaw.

9. The surgical device of claim 7, where the actuating jaw includes an opening at a distal portion thereof to expose the suture carrying slot when the jaw assembly is closed.

10. The surgical device of claim 1, wherein the second actuator includes a first extension pivotally coupled to the handle portion and a second extension pivotally coupled to the first extension, where the second extension includes a locking surface moveably engageable with a locking surface on the handle portion, such that when engaged, the locking surfaces locks the jaw assembly.

11. The surgical device of claim 1, wherein the curved needle includes a member that is disposed within a slot of the third actuator.

12. The surgical device of claim 1, wherein the first actuator is spring biased against the handle portion to maintain the curved needle within the curved track when the surgical device is at rest.

13. The surgical device of claim 1, wherein the curved needle is comprised of stainless steel.

14. The surgical device of claim 1, wherein the curved needle has a rectangular cross-sectional profile.

15. The surgical device of claim 1, wherein the shaft includes a port that permits fluids to pass through the shaft and toward the jaw assembly.

16. A suture passing instrument comprising:
a shaft having a proximal end and a distal end;
a handle assembly located at the proximal end of the shaft and including a needle actuator moveably coupled to a handle portion, a trigger lever moveably coupled to the handle portion, the handle portion coupled to the proximal end of the shaft;
a jaw assembly including an actuating jaw moveably coupled to a fixed jaw, the fixed jaw located at the distal end of the shaft, wherein actuation of the trigger lever moves the actuating jaw relative to the fixed jaw to open and close the jaw assembly;
a curved needle comprised of stainless steel and slidable within a curved needle track of the fixed jaw, wherein the curved needle track is defined by curved top and bottom surfaces that substantially match a curvature of the curved needle to permit movement of the curved needle through the curved track without being deformed, the curved needle having a suture carrying slot at a distal portion; and
a needle linkage having a first end coupled to a proximal section of the curved needle at a pivot joint and a second end coupled to the needle actuator, such that movement of the needle actuator advances the needle linkage to move the curved needle through the curved track without deforming the curved needle, where the pivot joint permits proximal-distal movement and superior-inferior movement of a distal end of the needle actuator.

17. The suture passing instrument of claim 16, wherein the substantially matched curvatures of the curved needle and the curved needle track permit movement of the curved needle through the curved track without deformation of the curved needle.

18. The suture passing instrument of claim 16, wherein the needle actuator includes a wider proximal region that tapers to a narrower distal region.

19. The suture passing instrument of claim 16, where the fixed jaw includes an opening at a distal end exposing the suture carrying slot for loading of the suture external to the shaft.

20. The suture passing instrument of claim 19, wherein the opening has a mouth at a side surface of the fixed jaw.

* * * * *